United States Patent [19]

Italiano et al.

[11] Patent Number: 4,524,605
[45] Date of Patent: Jun. 25, 1985

[54] POROSIMETER WITH DETECTION BY CAPACITY VARIATIONS

[75] Inventors: Pietro Italiano, Cernusco S/Naviglio; Ermete Riva, Merate, both of Italy

[73] Assignee: Carlo Erba Strumentazione S.p.A., Italy

[21] Appl. No.: 545,947

[22] Filed: Oct. 27, 1983

[30] Foreign Application Priority Data

Nov. 4, 1982 [IT]  Italy ................................ 24076 A/82

[51] Int. Cl.³ ............................................. G01N 15/08
[52] U.S. Cl. ........................................................ 73/38
[58] Field of Search ............................................ 73/38

[56] References Cited

U.S. PATENT DOCUMENTS 4,272,983  6/1981  Sisti et al. ................................ 73/38

Primary Examiner—Stewart J. Levy
Assistant Examiner—Joseph W. Roskos
Attorney, Agent, or Firm—Lerner, David, Littenberg, Krumholz & Mentlik

[57] ABSTRACT

The invention relates to a mercury porosimeter, of the type in which the quantity of mercury which has penetrated into the pores of the substance to be analyzed is determined by measuring capacity variations in a cylindrical condenser, the inner armature of which consists of the mercury present in the capillary of a penetrometer containing the substance to be analyzed, the penetrometer being housed inside an autoclave. The porosimeter according to the invention is characterized in that the outer armature of the condenser is fixed to the autoclave body, in that the condenser dielectric is formed by the penetrometer capillary and by the oil introduced into the autoclave to transmit pressure variations to mercury, and in that said oil has the same dielectric constant as the glass forming the penetrometer capillary.

13 Claims, 2 Drawing Figures

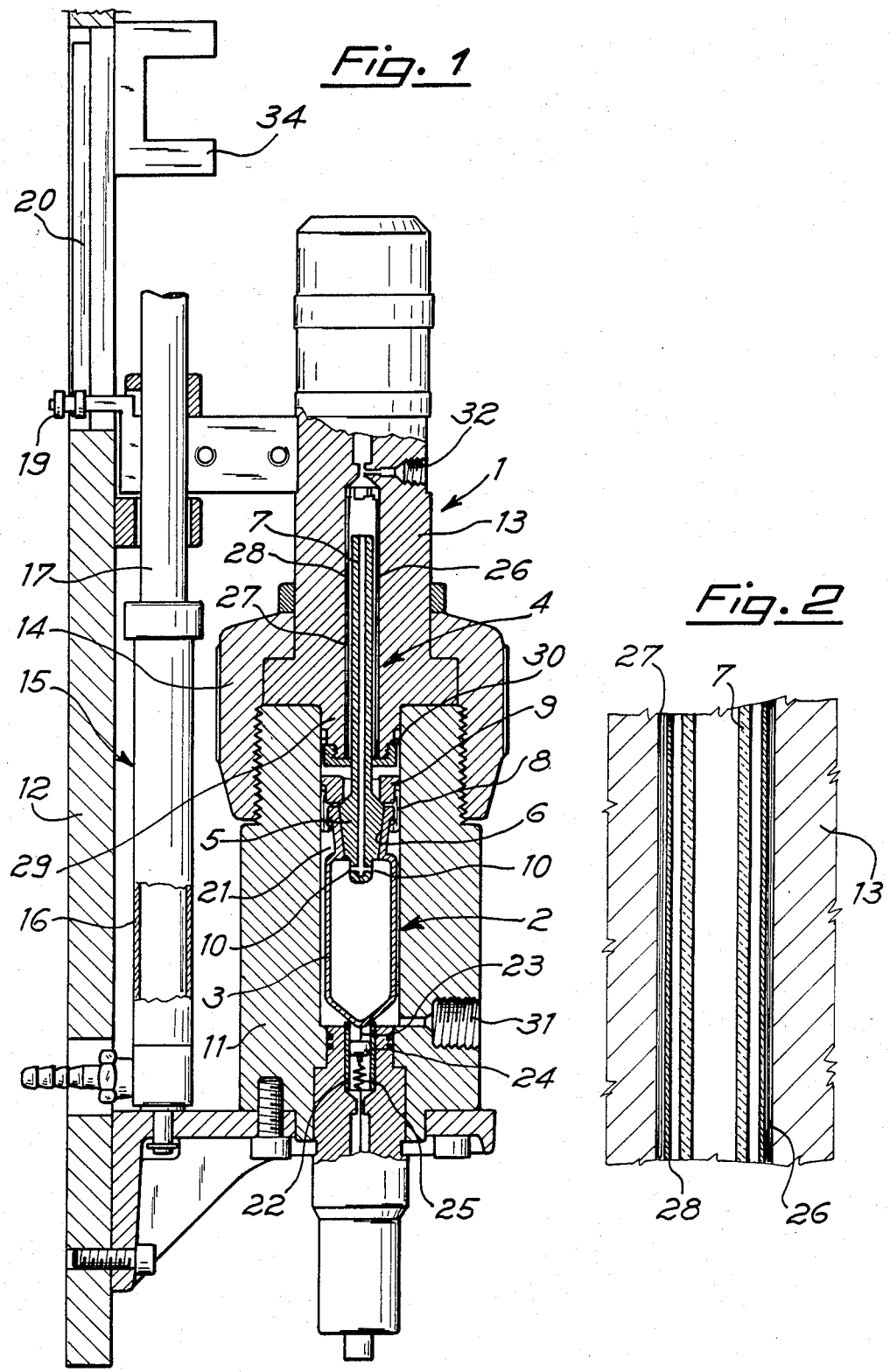

POROSIMETER WITH DETECTION BY CAPACITY VARIATIONS

BACKGROUND OF THE INVENTION

1. Field of the Invention

The present invention relates to an apparatus for porosimetric measurements, that is to measure the volume and size of microcavities present on the surface of a solid substance.

Said measurement is performed according to Drake method which essentially consists in placing a sample of the solid under test in a vessel, creating vacuum in said vessel, filling same with mercury and submitting mercury to ever increasing pressures. For each determined value of the pressure exerted on mercury, it is possible to establish, by means of a known formula, the pore average radius.

The biunivocal correlation between the pore volume and the relevant average radius is obtained by performing, for each value of pressure and therefore of the average radius, a detection of the volume variations of mercury present in the vessel. In fact, as this liquid is incompressible, each decrease in mercury volume which can be recorded outside corresponds to the introduction of an equal quantity of mercury into the sample pores.

2. Description of the Prior Art

In an actual application of said method, the vessel consists of a glass ampoule, or penetrometer, provided with an upwardly extending capillary and housed in an autoclave into which a liquid is introduced at ever increasing pressures, said liquid penetrating also partly into the ampoule mouth.

According to a known technique (U.S. Pat. No. 4,272,983) the detection of mercury volume variations in the penetrometer can be advantageously performed by recording the capacity variations of a cylindrical condenser, the internal armature of which is constituted by the same mercury contained in the capillary of said penetrometer, the dielectric is constituted by the capillary walls and the external armature is constituted by a metal lamina wound up around the external walls of the capillary. The capacity variations of such condenser, corresponding to the variations of its internal armature due to variations of the mercury meniscus level in the capillary, are proportional to the mercury volume penetrated, for a given pressure, into the pores of the solid sample under test.

According to this technique the variations of mercury volume and hence the determination of the pore volume are measured with very high precision and by means of a simple and functional device.

However, it has been noticed that the unavoidable size differences existing between a penetrometer and another one affect the value of their dielectric constant, which therefore results to be different for each penetrometer used. This difference between dielectric constants represents an important drawback considering that, in order to allow the performance of several subsequent analyses without being forced to empty and clean the penetrometer for each new analysis, different penetrometers are used, for each of them being therefore necessary to know the value of the dielectric constant. Moreover, each time a penetrometer is inserted into the autoclave it is necessary to perform heavy calibrations of the measuring apparatuses according to the value of the dielectric constant characteristic of said specific penetrometer.

The difference between the values of the dielectric constants is due to the difficulty of manufacturing penetrometers having capillaries with perfectly identical thickness, as well as to the difficulty of surperfectly rounding and in the same way the capillaries with the metal lamina forming the condenser armature. in particular the metal lamina does not always completely adhere to the external wall of the capillary and the different empty spaces created between the lamina and capillary of each penetrometer affect the value of its dielectric constant. Furthermore, such condenser, involving the need of obtaining penetrometers having perfectly calibrated thickness of capillary wall and internal diameter, is considerably expensive and increases the operating costs of the porosimeter.

OBJECTS OF THE INVENTION

An object of the present invention is to propose a new type of condenser and in particular a new configuration of the external armature of same, which allows the use of penetrometers having always the same value of dielectric constant, so as to warrant interchangeability without continuous and heavy calibrations of the measuring apparatuses.

Another object of the present invention is to semplify the penetrometer configuration with subsequent advantages for the operating costs of the porosimeter.

SUMMARY OF THE INVENTION

Accordingly this invention relates to an apparatus for porosimetric measurements which exploits the capacity variations of a cylindrical condenser whose variable inner armature is formed by the mercury contained in the capillary of the penetrometer where the sample to be analysed is housed, wherein the outer armature of said condenser is fixed to the autoclave body, wherein the condenser dielectric is formed by the penetrometer capillary and by the oil introduced into the autoclave to transmit pressure variations to mercury and wherein said oil has the same dielectric constant as the material forming the penetrometer capillary.

Said arrangement of the condenser outer armature and the use of an oil having the same dielectric constant as the material forming the penetrometer capillary allow to obtain the same electric behaviour with any penetrometer, provided that the inner diameter of the capillary is calibrated. As a matter of fact, being the condenser outer armature always the same for any penetrometer and in a fixed position with respect to the inner armature, it is sufficient that the inner diameter of the capillary is equal for all penetrometers to obtain that the oil, as used to transmit pressure variations to mercury, compensate for the possible differences in the capillary thickness and outer diameter and maintains the value of the condenser dielectric constant always the same. In this way the penetrometers result perfectly interchangeable, with the only condition that the inner diameter of the capillary is always the same, which condition is easily achievable, and the initial operations of calibration of the measuring apparatuses are eliminated. Furthermore, the arrangement of the outer armature according to the invention makes the penetrometer much cheaper and easier to be obtained, in that it needs no external metal coating and capillary walls of calibrated thickness.

BRIEF DESCRIPTION OF THE DRAWINGS

FIG. 1 is an axial section of an autoclave with penetrometer, ready for carrying out porosimetric measurements.

FIG. 2 is a magnified detail of FIG. 1 showing the condenser outer armature and the position of the capillary and mercury inside same.

First of all with reference to FIG. 1, the porosimeter is essentially formed by an autoclave 1 inside which a penetrometer 2 is placed containing the sample to be analysed and completely filled with mercury. The penetrometer 2 is constituted by a lower part 3 forming a vessel suitable for receiving the sample and by an upper part 4 closing said lower part 3. The upper part 4 comprises a base 5 having a truncated-cone shaped longitudinal section suitable for being inserted into the conical opening 6 of the lower vessel-section 3 and a capillary 7 upwardly extending and communicating with said vessel-section 3.

In particular, the capillary 7 communicates with the vessel 3 through two radial holes 10 which prevent samples having lower specific weight than mercury from entering into the capillary 7 while the penetrometer is filled with mercury.

A sealing between the two sections 3 and 4 forming the penetrometer is ensured by reciprocal screwing of a locking nut 8 and a ring 9 acting on the neck of the vessel-section 3 and on the base of the upper section 4 respectively.

According to said U.S. Pat. No. 4,272,983, the penetrometer 2 is housed in the autoclave 1 with the capillary 7 turned upwards in order to take full advantage of said position.

The autoclave 1 is formed by a lower part 11 fixed to a supporting element 12 and by a head 13 constituting the lid of the autoclave and which can be fixed to the lower part 9 by means of a threaded nut 14.

The head 13 of the autoclave is connected to the supporting element 12 by means of a longitudinally sliding damping element 15, which only allows movements controlled by said head 13. In particular, the damping element 15 comprises a sleeve 16 fixed to the supporting element 12 in which a rod 17 axially slides, said rod being provided with an arm supporting the autoclave head 13 and with a pivot 19 inserted into a turned up L-shaped guide 20 provided in the supporting element 12.

The penetrometer vessel part 3 is inserted with a little clearance into a hole 21 provided in the lower part of the autoclave 1 and rests with its cone-shaped lower end on a cyclindrical support 22 provided in the lower end of hole 21.

In correspondence to the cone vertex, the penetrometer vessel part 3 presents an electrode 23 which is electrically connected to measuring apparatuses of the porosimeter by means of a contact element 24 which is pushed against the electrode 23 by a spring 25.

The autoclave upper part 4 presents a hole 26, on the walls of which, with the interposition of a sheath made of electrically insulating material 27, a cylindrical metal lamina 28 is fixed having an internal diameter slightly exceeding the external diameter of the penetrometer cpaillary 7 (FIG. 2). The metal lamina 28 is electrically connected to the measuring apparatuses of the porosimeter and forms the fixed outer armature of a cylindrical condenser. The internal lower end of the autoclave lid 13 comprises a cylindrical part extending downwards and suitable for being inserted with a little clearance into the hole 21 of the autoclave lower part.

A ring gasket 30 housed in a suitable seat of the cylindrical part 29 ensures sealing between the upper part 13 and the lower part 11 of the autoclave. The autoclave lower part 11 is provided with a duct 31 equipped with a two-way valve (not illustrated) for supplying and discharging oil, in order to transmit pressures to the mercury contained in the penetrometer, while the autoclave upper part 13 is provided with a duct 32 and a valve (not illustrated) for bleeding the air contained in the autoclave when the same is filled with oil.

When the autoclave 1 is opened, by unscrewing the nut 14 and lifting the lid 13, the group formed by the pivot 19 and guide 20 prevents the lid 13 from rotating around the rod 17 axis of the damping element 15, which could damage that part of the capillary 7 protruding from the lower part of the autoclave. When the lid 4 is sufficiently far from the capillary 7, the horizontal part of the guide 20 lets the lid itself to rotate around the rod 17 axis in order to allow removal of the penetrometer from the autoclave lower part. A support 34, which matches the arm of the autoclave lid, keeps the lid itself in the opening position of the autoclave. When the autoclave is closed, the damping element 15 causes a braked descent of the lid 13, which has a considerable weight, while the pivot 19-guide 20 group maintains the lid itself perfectly centered with respect to the autoclave lower part 11 so that the capillary 7 penetrates without any difficulty or breaking danger into the hole 26 and along the metal lamina 28.

The little clearance existing between the penetrometer vessel part 3 and the walls of the hole 21 of the autoclave lower part together with the penetrometer cone-shaped lower end resting on the cylindrical support 22 allow correct centering of the penetrometer inside the autoclave.

It must be noticed that, though a preferred embodiment of the invention has been illustrated and described, however it may undergo to numerous changes and variations, as it will be obvious to those skilled in the art, without departing from the spirit and the scope of the present invention.

We claim:

1. An apparatus for porosimetric measurements by recording capacity variations in a cylindrical condenser, said apparatus comprising a porosimeter penetrometer for housing a sample to be analyzed, said penetrometer including a capillary with a capillary wall having an outer surface and an inner surface, with said inner surface defining a predetermined inner diameter for said capillary, whereby when mercury is contained in said capillary, said mercury forms a variable inner armature for said condenser; and a porosimeter autoclave body for housing said porosimeter penetrometer, said porosimeter autoclave body including a fixed outer armature for said condenser mounted thereon, said fixed outer armature being mounted such that, when said penetrometer is housed in said porosimeter autoclave body, a uniform spacing is provided between said fixed outer armature and said capillary inner surface and a space is provided between said fixed outer armature and said capillary outer wall, whereby an oil having a dielectric constant the same as the dielectric constant of the capillary wall may be introduced into said space and said oil and said capillary wall can form a condenser dielectric for said condenser.

2. An apparatus for porosimetric measurements according to claim 1, wherein said penetrometer is housed in the autoclave body with the capillary upwardly directed.

3. An apparatus for porosimetric measurements according to claim 1 or 2, wherein the autoclave body comprises a lower part where said penetrometer is housed and an upper part airtightly connectable to the lower part, the fixed outer armature of said condenser being mounted inside said autoclave body upper part.

4. An apparatus for porosimetric measurements according to claim 3, wherein the upper part of said autoclave body is fixed to a damping element which allows controlled movements of the upper part of the autoclave body along a path parallel to the longitudinal axis of the autoclave body between a lower position where the upper part of the autoclave body is in contact with said lower part of the autoclave body and an upper position, and wherein said damping element allows controlled movement of the upper part of the autoclave body along a path perpendicular to said axis when said autoclave body upper part is in said upper position.

5. An apparatus for porosimetric measurements according to claim 4, wherein the upper part of the autoclave body in correspondence to the connecting surface with the autoclave body lower part has an axial duct into which the penetrometer capillary penetrates and on the inner walls of which duct the condenser fixed outer armature is mounted.

6. An apparatus for porosimetric measurements according to claim 2, wherein the penetrometer has a cone-shaped lower end and wherein said lower end rests inside the autoclave body on a concave support provided inside the lower part of the autoclave body itself.

7. An apparatus according to claim 1, wherein said porosimeter autoclave body includes means for introducing an oil to said space and to said cappillary for transmitting pressure variations to said mercury.

8. An apparatus for porosimetric measurements by recording capacity variations in a cylindrical condenser, said apparatus comprising a porosimeter penetrometer including a capillary having a capillary wall with an outer surface and inner surface, and inner surface defining a predetermined inner diameter for said capillary; a sample to be analyzed housed in said penetrometer; mercury in contact with said sample in said penetrometer and forming in said capillary a variable inner armature for said condenser; a porosimeter autoclave body housing said porosimeter penetrometer; a fixed outer armature for said condenser mounted on said said autoclave body such that a uniform spacing is provided between said fixed outer armature and said inner surface of said capillary wall and a space is provided between said fixed outer armature and said outer surface of said capillary; and means for introducing an oil having the same dielectric constant as said capillary wall to said space and to said capillary for transmitting pressure variations to said mercury, wherein said oil and said capillary wall form a condenser dielectric for said condenser.

9. A method for making porosimetric measurements by recording capacity variations in a cylindrical condenser, said method comprising the steps of providing a porosimeter penetrometer for housing a sample to be analyzed, said penetrometer including a capillary having a capillary wall with an outer surface and an inner surface, said inner surface defining a predetermined inner diameter for said capillary; introducing a sample into said penetrometer; introducing mercury into said penetrometer and said capillary, whereby said mercury forms a variable inner armature for said condenser; placing said porosimeter penetrometer into an autoclave body including a fixed outer armature for said condenser mounted thereon and said outer armature being mounted so as to provide a space between said fixed outer armature and said outer surface and a uniform spacing between said fixed outer armature and said inner surface; introducing an oil having the same dielectric constant as said capillary wall into said porosimeter autoclave body to transmit pressure variations to said mercury and into said space between said outer armature and said outer wall of said capillary, so that said oil and said capillary wall form a condenser dielectric for said condenser; and measuring variations in capacitance of said condenser as said mercury in said capillary varies with the pressure provided by the introduced oil.

10. A method according to claim 9, wherein said penetrometer is housed in the autoclave body with the capillary upwardly directed.

11. A method according to claim 9 or 10, wherein the autoclave body comprises a lower part where the penetrometer is housed and an upper part airtightly connecting to the lower part, wherein the outer armature of the condenser is mounted inside the autoclave body upper part.

12. A method according to claim 11, wherein the upper part of the autoclave body in correspondence to the connecting surface of the autoclave body lower part has an axial duct into which the penetrometer capillary penetrates and on the inner walls of which duct the condenser outer armature is mounted.

13. A method according to claim 11, wherein the penetrometer has a cone-shaped lower end and wherein said penetrometer is placed in said autoclave body so that said lower end rests on a concave support provided in the lower part of the autoclave body.

* * * * *